US012251552B2

(12) United States Patent
Apollonio et al.

(10) Patent No.: US 12,251,552 B2
(45) Date of Patent: Mar. 18, 2025

(54) FLEXIBLE ELECTRODE FOR APPLYING AN ELECTRIC FIELD TO THE HUMAN BODY

(71) Applicant: Rise Technology S.R.L., Rome (IT)

(72) Inventors: Francesca Apollonio, Rome (IT); Marco Balucani, Rome (IT); Dario Bernardi, Rome (IT); Ruggero Cadossi, Rome (IT); Agnese Denzi, Rome (IT); Micaela Liberti, Rome (IT); Donata Marazzi, Rome (IT); Paolo Marracino, Rome (IT); Roberto Pagliucci, Rome (IT); Mattia Ronchetti, Rome (IT)

(73) Assignee: Rise Technology S.R.L., Rome (IT)

( * ) Notice: Subject to any disclaimer, the term of this patent is extended or adjusted under 35 U.S.C. 154(b) by 0 days.

(21) Appl. No.: 16/071,069

(22) PCT Filed: Jan. 17, 2017

(86) PCT No.: PCT/IB2017/050236
§ 371 (c)(1),
(2) Date: Jul. 18, 2018

(87) PCT Pub. No.: WO2017/125848
PCT Pub. Date: Jul. 27, 2017

(65) Prior Publication Data
US 2019/0060631 A1    Feb. 28, 2019

(30) Foreign Application Priority Data
Jan. 18, 2016   (IT) .................. 102016000004063

(51) Int. Cl.
*A61N 1/04*    (2006.01)
*A61N 1/32*    (2006.01)
*A61N 1/36*    (2006.01)

(52) U.S. Cl.
CPC ......... *A61N 1/0412* (2013.01); *A61N 1/0452* (2013.01); *A61N 1/0472* (2013.01);
(Continued)

(58) Field of Classification Search
CPC ... A61N 1/0472; A61N 1/327; A61N 1/36014
See application file for complete search history.

(56) References Cited

U.S. PATENT DOCUMENTS 5,128,257 A * 7/1992 Baer .................... C07K 14/495
                                               435/173.6
5,318,514 A * 6/1994 Hofmann ............... A61N 1/327
                                                   604/20
(Continued)

FOREIGN PATENT DOCUMENTS

| WO | 0181532 A1 | 11/2001 |
| WO | 2013167185 A1 | 11/2013 |
| WO | 2017125848 A1 | 7/2017 |

OTHER PUBLICATIONS

International Searching Authority; "Writtein Opinion of the International Searching Authority and International Search Report from PCT Application No. PCT/IB2017/050236 mailed Jul. 27, 2017"; from Foreign Counterpart of U.S. Appl. No. 16/071,069; pp. 1-9; Dated Jul. 27, 2017; Published: EP.

(Continued)

Primary Examiner — Rex R Holmes
Assistant Examiner — Jennifer L Ghand
(74) Attorney, Agent, or Firm — Bryan A. Santarelli; FisherBroyles, LLP (57) ABSTRACT

A flexible electrode (1) for applying an electric field to the human body, comprising: a gripping portion (3); a deformable structure (5) having a first face (5a) fixed to the gripping portion (3); a flexible polymeric film (7) arranged on a flat second face (5b) of the deformable structure (5) and provided, on a flat face (7a) thereof facing outwards the
(Continued)

electrode (1), with flat metal structures (10,11) defining at least one first electrode and one second electrode (A,B), surfaces (10a,11a) of the flat metal structures (10,11) facing outwards the polymeric film (7) being coplanar with the flat face (7a) of the polymeric film (7).

19 Claims, 7 Drawing Sheets

(52) U.S. Cl.
CPC .......... *A61N 1/0492* (2013.01); *A61N 1/327* (2013.01); *A61N 1/36014* (2013.01)

(56) References Cited

U.S. PATENT DOCUMENTS

| | | | | |
|---|---|---|---|---|
| 5,911,223 | A * | 6/1999 | Weaver | A61N 1/0424 128/898 |
| 8,337,493 | B2 * | 12/2012 | Sohn | A61N 1/327 606/45 |
| 2004/0267189 | A1 * | 12/2004 | Mavor | A61N 1/044 604/20 |
| 2006/0036209 | A1 * | 2/2006 | Subramony | A61M 37/0015 604/20 |
| 2008/0208107 | A1 * | 8/2008 | McRae | A61N 1/0428 604/20 |
| 2010/0022864 | A1 * | 1/2010 | Cordero | A61B 5/291 600/372 |
| 2010/0179455 | A1 * | 7/2010 | Nebrigic | A61B 18/18 606/33 |
| 2011/0178518 | A1 * | 7/2011 | Sohn | A61N 1/0424 606/41 |
| 2011/0193362 | A1 * | 8/2011 | Prahlad | B25J 15/0085 294/81.2 |
| 2014/0104744 | A1 * | 4/2014 | Prahlad | B25J 15/0085 361/234 |
| 2019/0060631 | A1 * | 2/2019 | Apollonio | A61N 1/0452 |

OTHER PUBLICATIONS

Wei, Zewen et al. "A Flexible microneedle array as low-voltage electroporation electrodes for in vivo DNS and siRNA deliver"; Lab On a Chip: Miniaturisation for Chemistry, Physics, Biology, Materials Science and Bioengineering; vol. 14, No. 11; Date: Aug. 11, 2014; pp. 4093-4102.

European Patent Office, "Communication pursuant to Article 94(3) from U.S. Appl. No. 16/071,069", from Foreign Counterpart to U.S. Appl. No. 16/071,069, Oct. 17, 2019, pp. 1-3, Published: EP.

International Bureau, "International Preliminary Report on Patentability from PCT Application No. PCT/IB2017/050236", from Foreign Counterpart to U.S. Appl. No. 16/071,069, filed Aug. 2, 2018, pp. 1 through 7, Published: WO.

International Searching Authority, "International Search Report and Written Opinion from PCT Application No. PCT/IB2017/050236", from Foreign Counterpart to U.S. Appl. No. 16/071,069, filed May 10, 2017, pp. 1 through 14, Published: WO.

* cited by examiner

FLEXIBLE ELECTRODE FOR APPLYING AN ELECTRIC FIELD TO THE HUMAN BODY

TECHNICAL FIELD

The present disclosure relates to a flexible electrode for applying an electric field to the human body.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

As it is known, the application of electrical fields to the human body is performed by electronic devices adapted to output a pulsing alternated signal (for example, mono- or bi-polar pulses) by supplying a plurality of electrodes applied to a portion of the human body for inducing a pulsed electric field within the tissue surrounding the application position.

The electric field created may advantageously be used to modify the permeability of the cell membrane of the cells begin present in the tissue itself (electroporation process). In this case, the change of the permeability of the cell membrane is used to convey molecules such as drugs, organic and/or genic compounds. The electric field may also be used for different purposes, for example, to perform a muscle stimulation.

Figure 11:
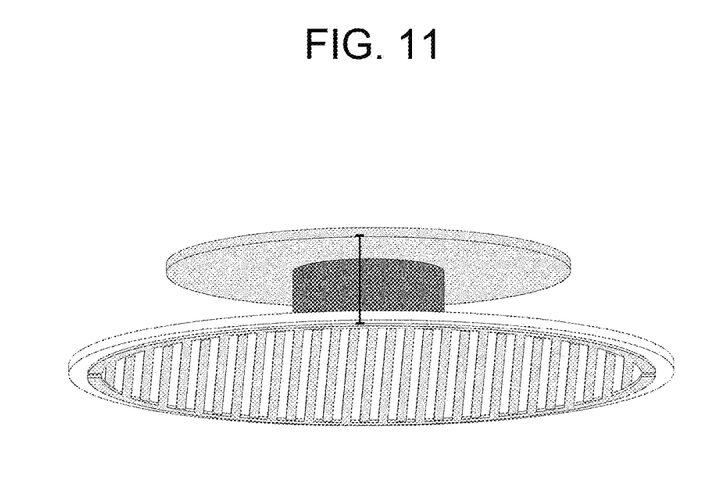
FIG. 11 illustrates an electrode according to the prior art.

An example of electrode according to the prior art is described in the patent application WO2013167185 wherein there is detailed (FIG. 11) an electrode for electroporation adapted to generate a pulsed electric field to perform a process of electroporation of a biologic sample that is grown on a culture substrate. The electrode is adapted to be positioned on the upper part of the biological sample avoiding a direct contact between the electrode and the biological sample. This electrode is produced by a manufacturing technique similar to that used in printed circuit boards and it comprises a flat substrate of non-conductive rigid material and a matrix of electrodes arranged on a first side of the flat substrate and forming at least two electrodes being spaced apart to each other.

In the patent application WO2013167185 there is specifically mentioned that the matrix of electrodes must not come into direct contact with the biological tissue unless the electrodes are covered with non-cytotoxic material such as, for example, gold or platinum.

The electrodes described in the patent application WO2013167185 do not arrange themselves completely in contact with the portion of the human body and the electric field begin produced does not have sufficient intensity and uniformity within the biological structure.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of using a flexible electrode.

Therefore, the electrode easily adapts to a portion of the human body, being it either concave or convex, in such a way to ensure, within the portion of the human body below the electrode, a sufficient field intensity to produce a process of electroporation, of muscle stimulation or of other electric stimulation of a tissue in the human body. The electrode according to the present disclosure also has a simple and robust structure.

Particularly, an aspect provides a flexible electrode for applying an electric field to the human body, characterized by comprising: a gripping portion; a deformable structure having a first face fixed to the gripping portion; a flexible polymeric film arranged on a flat second face of the deformable structure and provided, on a flat face thereof facing outwards the electrode, with flat metal structures defining at least one first electrode and one second electrode; the surfaces of the flat metal structures facing outwards the polymeric film being coplanar with the flat face of the polymeric film.

A further aspect provides an electroporation device comprising such flexible electrode.

A further aspect provides a corresponding method for producing the flexible electrode.

Particularly, in an embodiment the polymeric film is thermoplastic; in this case, the production of the flat metal structures comprises producing the flat metal structures being raised on the flat face of the polymeric film, pressing the polymeric film provided with the raised flat metal structures between heated flat molds being parallel to each other so that the flat metal structures penetrate into the polymeric film that deforms thermally thereby arranging coplanar with the flat face of the polymeric film.

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes—such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually.

Particularly.

DETAILED DESCRIPTION

Figure 1:
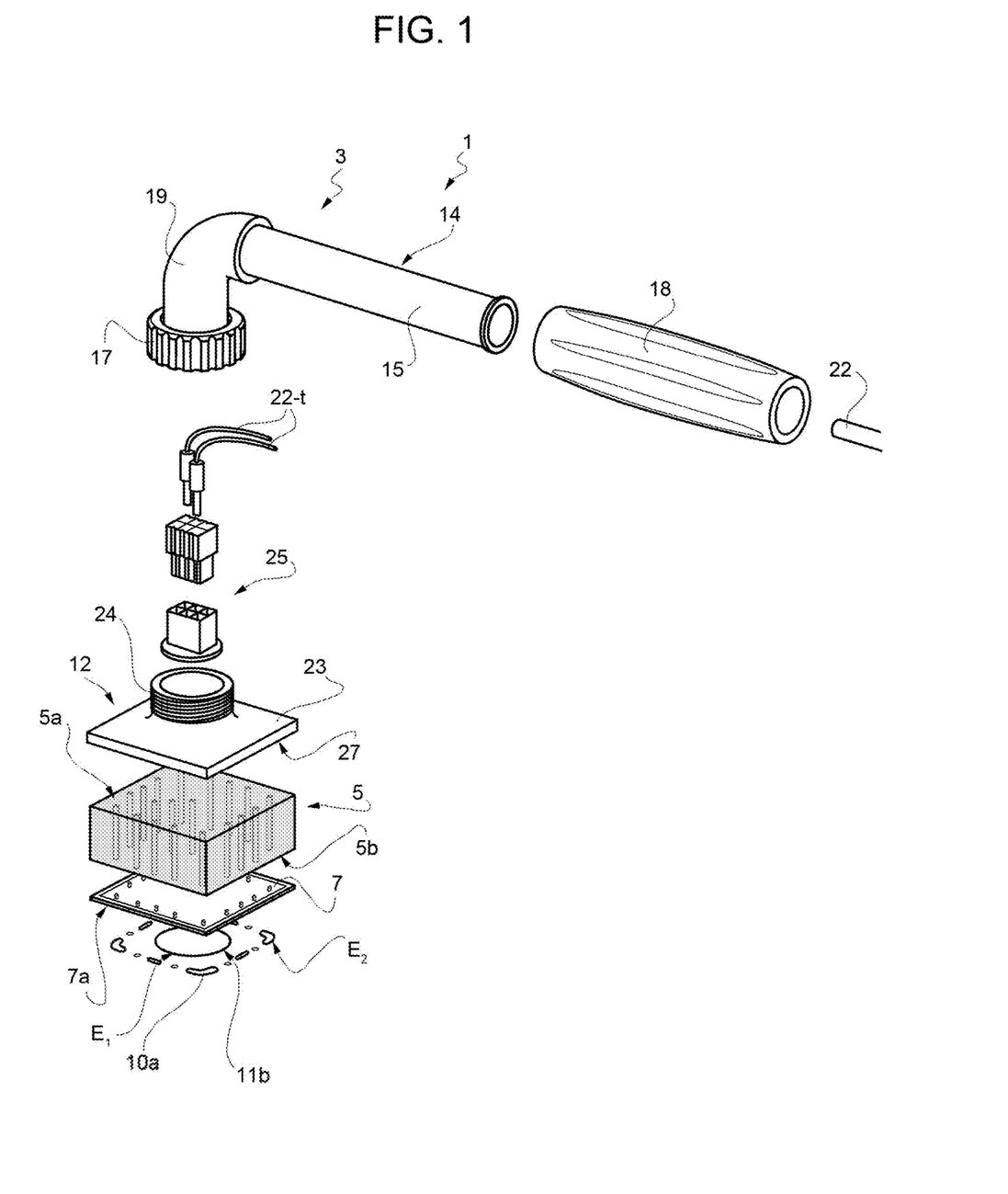
FIG. 1 illustrates, in exploded perspective view, a flexible electrode for applying an electric field to the human body according to the teachings of the present disclosure.

In FIG. 1 there is denoted with 1, as a whole, a flexible electrode for applying an electric field to the human body. Typically, but not exclusively, the electrode 1 is advantageously used in a process of electroporation during which an electric field is applied to a portion of human body (not shown). The electrode 1 may also be used in different fields, for example, for the muscle stimulation.

Figure 3:
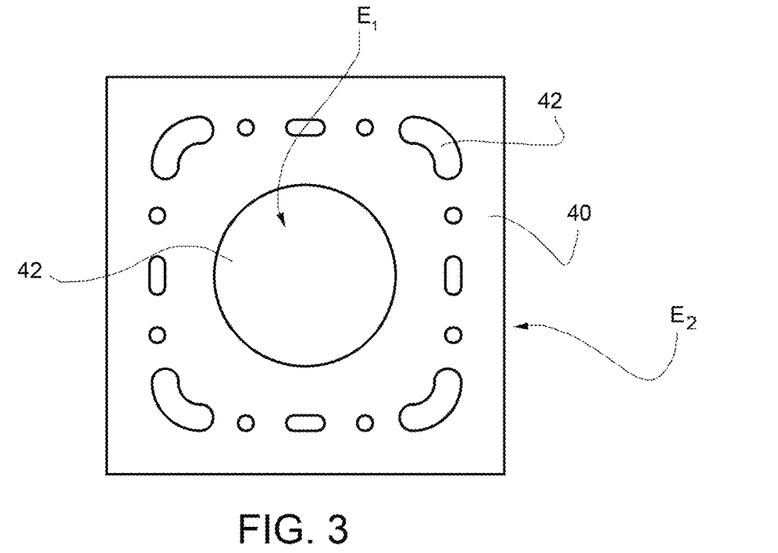
FIGS. 3 to 7 illustrate an example of a possible process for producing the electrode of FIG. 1.

The electrode 1 comprises a portion 3 of gripping type, a deformable structure, for example, a spongy structure/elastomeric structure having a first face 5a thereof fixed to the gripping portion 3, a flexible polymeric film 7 arranged on a second flat face 5b of the spongy/elastomeric structure 5 and provided, on a face facing outwards the electrode 1, with areas provided with flat metal structures defining at least one first electrode and one second electrode E1, E2 (see FIG. 3). The deformable structure might also be made by a flexible and compressible gel block (for example, silicone gel) or by silicone or any other elastomeric polymeric material of the thermosetting or thermoplastic type.

As will be detailed below (see also FIG. 2), the surfaces 10a, 10b of the flat metal structures 10, 11 facing outwards the polymeric film 7 are coplanar with the flat surface 7a of the polymeric film 7 facing outwards the electrode.

Returning to FIG. 1, in greater detail, the gripping portion 3 comprises a rigid support 12 that carries the spongy structure 5 and a handle 14 connected with the support 12 by a fixing ring nut 17. The handle 14 comprises a straight tubular portion 15 covered by a tubular sleeve 18 made of flexible material implementing a soft grip. The handle 14 further comprises an elbow tubular portion 19 that extends from a first end of the straight tubular portion 15 and that leads to a free end of the fixing ring nut 17. An electric cable 22 used to supply a signal to the electrodes E1, E2 extends from a second end of the tubular portion 15.

The rigid support 12 comprises a flat square wall 23 made of plastic material integral with a tubular body 24 that extends from a central portion of the wall 23 with its axis perpendicular to the plane of the wall 23. The tubular body 24 is threaded externally and it is adapted to mate with the ring nut 17 to make a stable connection between the handle 14 and the rigid support 12.

The tubular body 24 defines a cavity that, in use, communicates with the tubular portion 15 and that is used for housing a connector 25 used for connecting the conductors 22-t of the electric cable 22 with the flat metallic structures 10A, 11B that implement the electrodes E1 and E2. The cavity defined by the tubular body 24 opens onto a flat square wall 27 on which the first face 5a of the spongy structure 5 is firmly fixed (for example, glued).

The spongy/elastomeric structure 5 is shaped like a parallelepiped being delimited, inter alia, by the first square face 5a and by the square face 5b being parallel to the face 5a; in this way, the spongy/elastomeric structure 5 has thickness D (see FIG. 2) that is constant in a direction perpendicular to the laying plane of the first face 5a and of the second face 5b. The spongy/elastomeric material is, for example, made of expanded polypropylene and the thickness D of this material sets the limits of conformability of the flexible electrode 1. The thickness of the spongy structure 5 may vary between 0.05 cm and 10 cm, preferably 1-5 cm.

The polymeric film 7 is square and it is sized to completely cover the square face 5b of the spongy structure 5. Typically, the thickness d of the polymeric film 7 (see FIG. 2) is comprised from 0.2 to 5 mm. The film 7 is made of any thermoplastic material.

Figure 2:
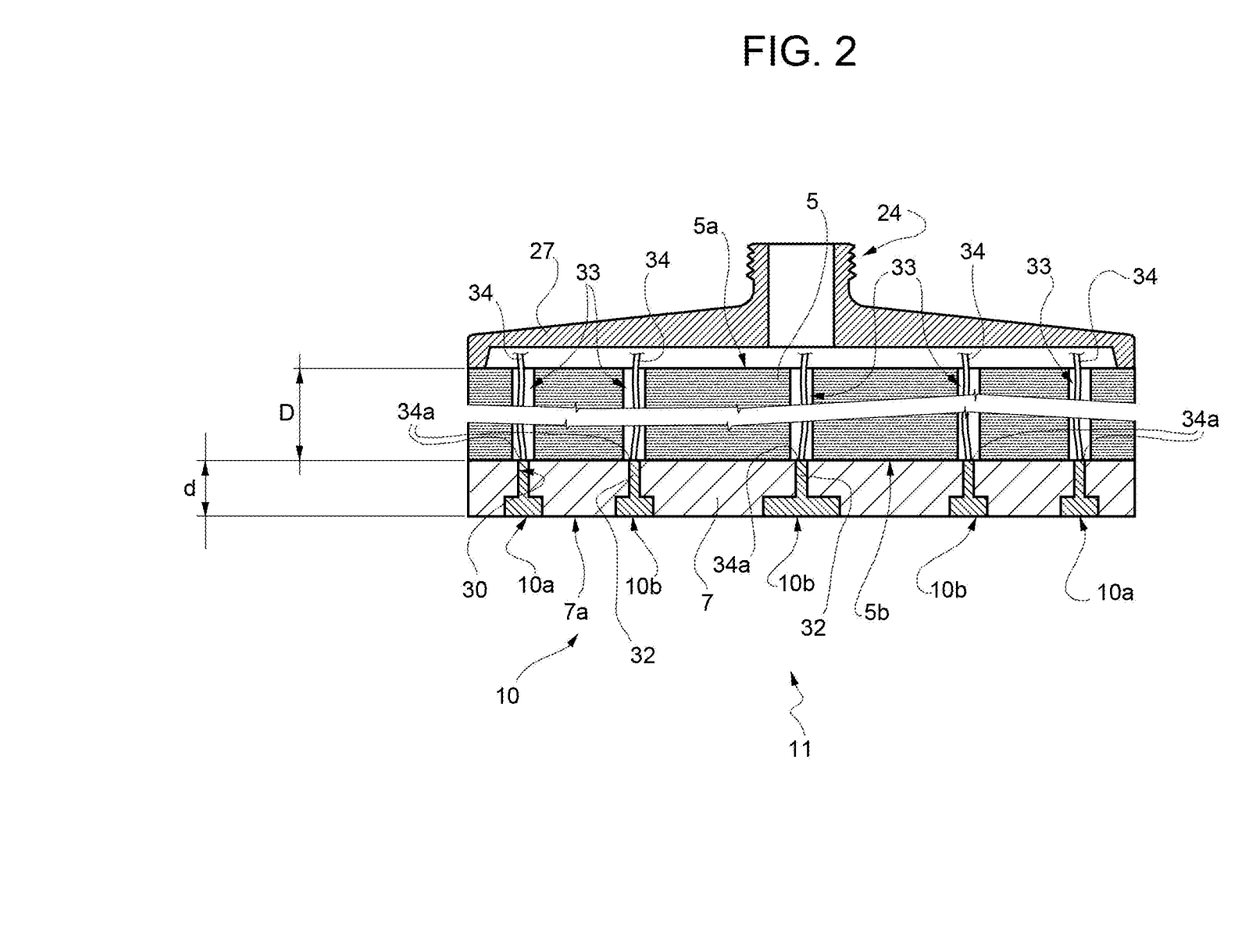
FIG. 2 illustrates, in cross section, the electrode of FIG. 1.

Turning to FIG. 2, the polymeric film 7 is provided with first through holes 30 engaged by through vias 32, or stems communicating electrically with the flat metal structure 10a, 11b implementing the electrodes E1 and E2 (see FIG. 1). The spongy/elastomeric structure 5 has a plurality of second through holes 33 aligned with the first through holes 30 and that accommodate thread-like electric conductors 34 having first ends 34a electrically interconnected with the stems 32 and second ends electrically communicating with the power supply cable 22 (see FIG. 1).

The electrode 1 according to the present disclosure self-adapts to the curved shape of the human body since the spongy/elastomeric structure 5 deforms thereby adapting to the surface of the human body and the film 7 arranges in direct and intimate contact with the surface of the human body, for example, but not exclusively the skin. The absolute coplanarity between the flat metal structures 10a, 11b that implement the electrodes E1 and E2 and the outer surfaces of the film 7 allows applying an electric field with high efficiency ensuring a good penetration of the field itself below the zone of application.

A non-limiting example will now be described of a process for producing the electrode.

At the beginning, a silk-screen printing plate 40 is prepared (FIG. 3), for example, of metal (steel), provided with through openings 42 that define the geometry of the electrodes E1, E2. An example of a square plate for performing the silk-screen printing is shown in FIG. 3.

Figure 4:
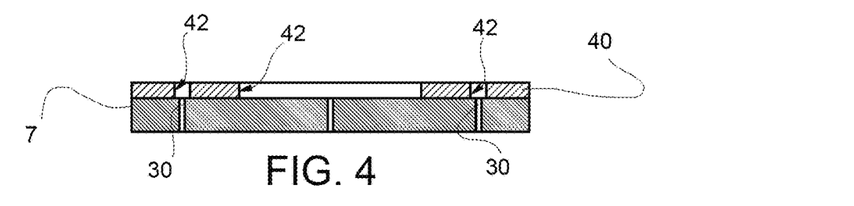

The silk-screen printing plate 40 is then superimposed (FIG. 4) and aligned above the thermoplastic polymeric film 7 provided with the through holes 30; the through holes 30, according to their size, may be made by machining if their diameter is higher than 0.3 mm or by laser if their diameter is lower than 0.3 mm. The silk-screen printing plate 40 has its through openings 42 arranged in correspondence to the holes 30 previously made on the film 7.

Figure 5:
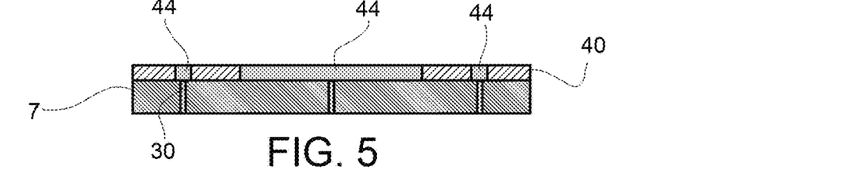

Subsequently, a metal paste 44 is spread (FIG. 5) onto the silk-screen printing plate 40 in such a way that this paste 44 penetrates into the through openings 42 of the silk-screen printing plate 40 and into the holes 30 of the film 7. For example, a silver paste (for example, the Ag paste 520 EI produced by Chimet S.p.A.) may be used.

The silk-screen printing plate 40 is removed and islands of metallic paste 44 (FIG. 6) remain on the film 7 that reproduce the perimeter of the openings 42 of the silk-screen printing plate 40. The thickness of each island is a function of the thickness of the silk-screen printing plate 40.

Figures 6, 7:
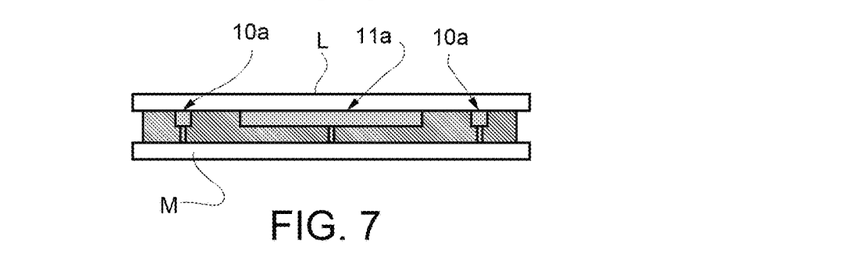

The film 7 provided with islands of metal paste is heated in oven (for example, at a temperature of 80° C. for about 40 minutes) so that the paste 44 cures and each island 44 transforms into a flat metal structure being raised on the film 7 and the past arranged in the through holes 30 forms the metallic stems.

Alternatively to what has been said before, the metal islands 44 might be made by a different process of deposition, for example, by using a three-dimensional printer capable of depositing a rigid conductive layer.

Once the metal islands 44 have been formed, they are covered by a galvanic process for depositing one or more metals in order to decrease the electrical resistance of the metal contacts and to passivate the silver paste. For example, the galvanic deposition may deposit 10 μm of copper and then 1 μm of gold, platinum, palladium or its alloys such as palladium-cobalt in order to passivate the metal surface and to reduce the anodic corrosion during the electroporation process.

The film 7 provided with the raised flat metal structures so obtained is pressed between two heated flat molds L, M being parallel to each other (FIG. 7) in such a way that the flat metallic structures penetrate the thickness of the film 7 that is deformed thermally. In this way (see again FIG. 1), the surfaces 10*a*, 11*a* of the flat metal structures facing outwards the polymeric film 7 arrange coplanar with the flat surface 7*a* of the polymeric film 7 that is leveled and smoothed by one of the two molds.

For example, it is enough to use the parameter denoted as "Vicat Softening Temperature" to know temperature and load (in Newton) to be applied to the thermoplastic film 7 in order to ensure that the flat metal structures penetrate within the polymer so as to have metal (silver paste) and polymer coplanar with each other. In the technical jargon this technique is called hot embossing.

The film 7 provided with flat metal structures is applied onto the second flat face 5*b* of the spongy/elastomeric structure 5 having the first face 5*a* fixed to a gripping portion, for example, the above-described gripping portion 3.

The metal stems 32 (see FIG. 2) are connected with electric conductors 34 that cross the spongy/elastomeric structure 5 and that communicate electrically with the signal supply cable 22.

Figure 8:
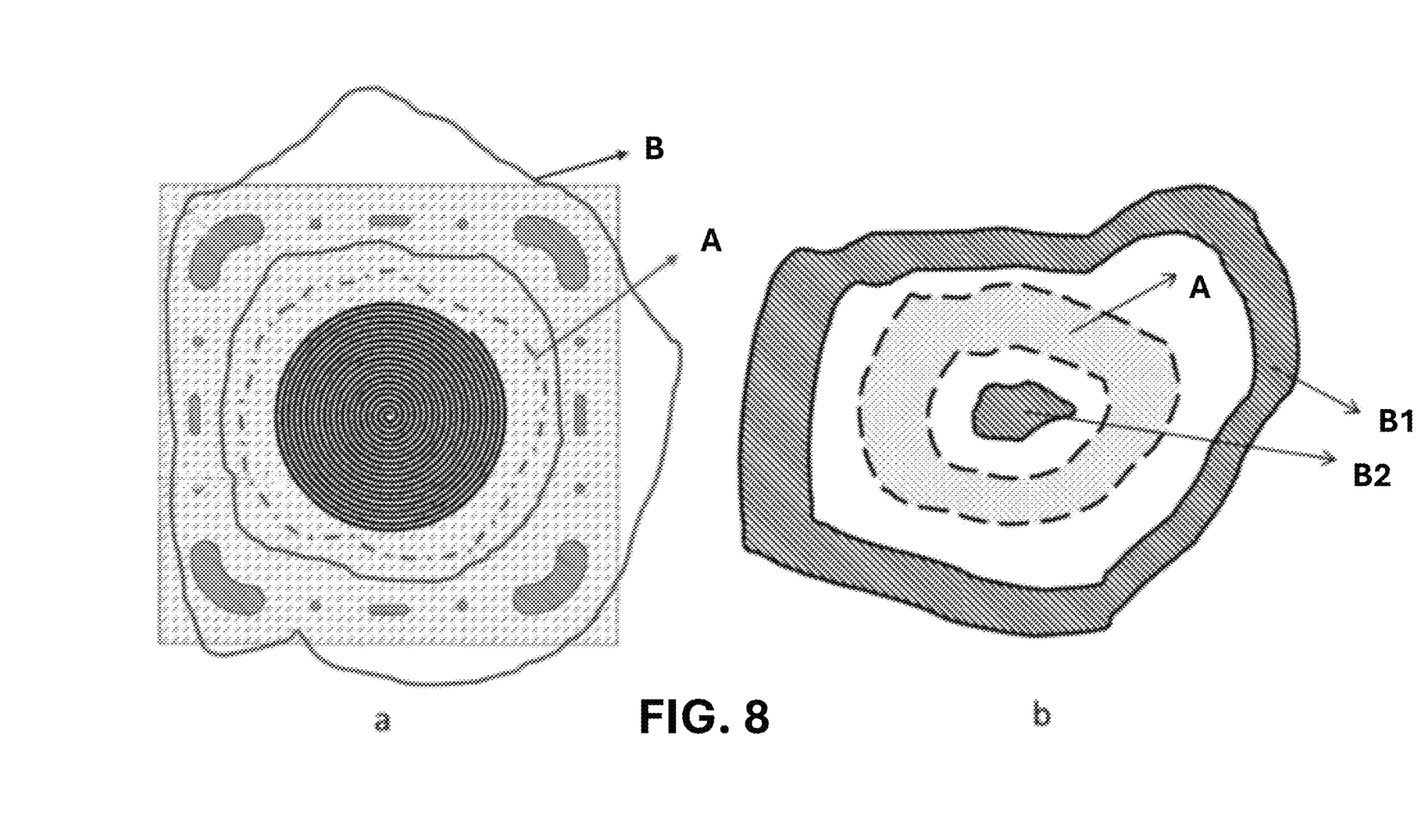
FIG. 8 exemplifies the operation of the electrode of FIG. 1.

According to another feature of the present disclosure, as shown in FIG. 8*a*, all the flat metal structures (10*a* in FIG. 1) belonging to a first area A are electrically connected to each other to be set to a common potential V1 whereas the flat metal structures (11*a* in FIG. 1) belonging to a second area B are electrically connected to each other to be set to a common second potential V2 different from the first potential; the second area B surrounds the first area A and without overlapping/intersecting with it. More than two areas may be provided, for example, three areas and namely an area B2 provided with flat metal structures (FIG. 8*b*) that is internal to the first area A and it does not overlap and does not intersect with the area A that, in the example, has flat metallic structures that extend along an annular-shaped path. A third area B1 is also provided that is external to the first area A and it does not overlap and does not intersect with the area A and it has flat metal structures that extend along an annular path that contains the annular path of the area A internally.

The third area B1 may be set to the potential V2 like the area B2 or to a third potential V3.

The configuration shown in FIG. 8*a* allows a higher penetration of the electric field within the tissue underlying the electrode.

For example, in FIG. 8*a* there is illustrated a continuous flat metal structure (first electrode) shaped like a spiral and contained in an area A with circular perimeter that is surrounded by a plurality of non-continuous flat metal structures (second electrode) contained in a second area B shaped like a square frame that encloses the circular area A.

The flat metal structures at polarity V1 may, for example, have a shape that is polygonal with any number of sides, circular, ellipsoidal, helical, spiral-like, based on rays of any shape, or any shape provided that it may be enclosed within a closed region (region A) that may be surrounded by at least one region B with which the region does not intersect.

Figure 9A:
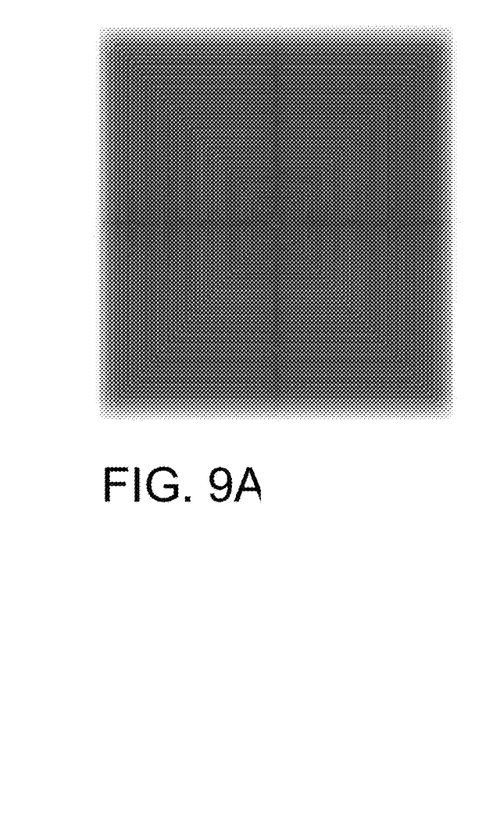
FIGS. 9a, 9b and 9c represent examples of implementation of a portion of the electrode.
Figure 9B:
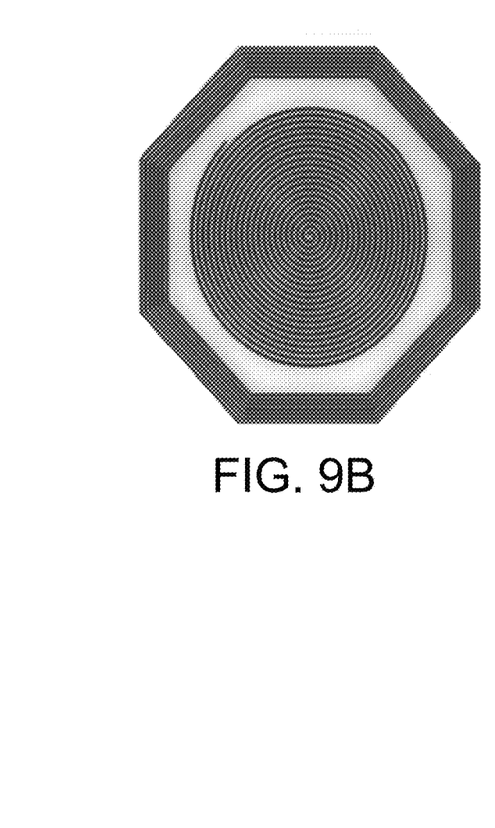
Figure 9C:
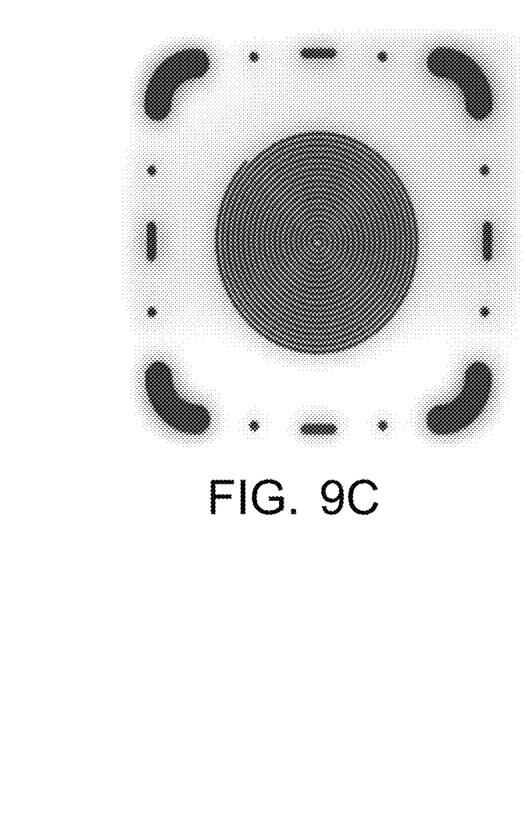

Examples of such geometries are shown in FIGS. 9*a*, 9*b* and 9*c*.

The geometry of FIG. 9*a* is formed by square-shaped concentric conductors, the most external ones and the central one are at potential V2, the intermediate conductors are at potential V1 (in this case there areas are present as illustrated in FIG. 8*b*).

In the geometry 9*b*) the flat metal structures at polarity V1 are spiral-shaped and the flat metal structures at polarity V2 are concentric octagons (in this case there are only two areas as illustrated in FIG. 8*a*).

In the geometry 9*c*) the flat metal structures at polarity V1 is spiral-shaped and the flat metal structures at polarity V2 are divided into some "islands" of metallization contained in an area shaped like a square frame (in this case as well there are only two areas).

The particular developed geometry allows obtaining values of electric field that exceed a given minimum value of the electric field (E>ETH) at different depths below the surface of the electrode for different values of applied voltage.

The present electrode may be used with an electroporation device provided with a pulse generator adapted to generate pulses with adjustable width in order to change the value of the electric field created in the tissue in such a way that the value of the generated electric field exceeds the threshold value, for example, equal to 20 KV/m, in a convex area that penetrates by at least 1 cm within the tissue.

Figure 10:
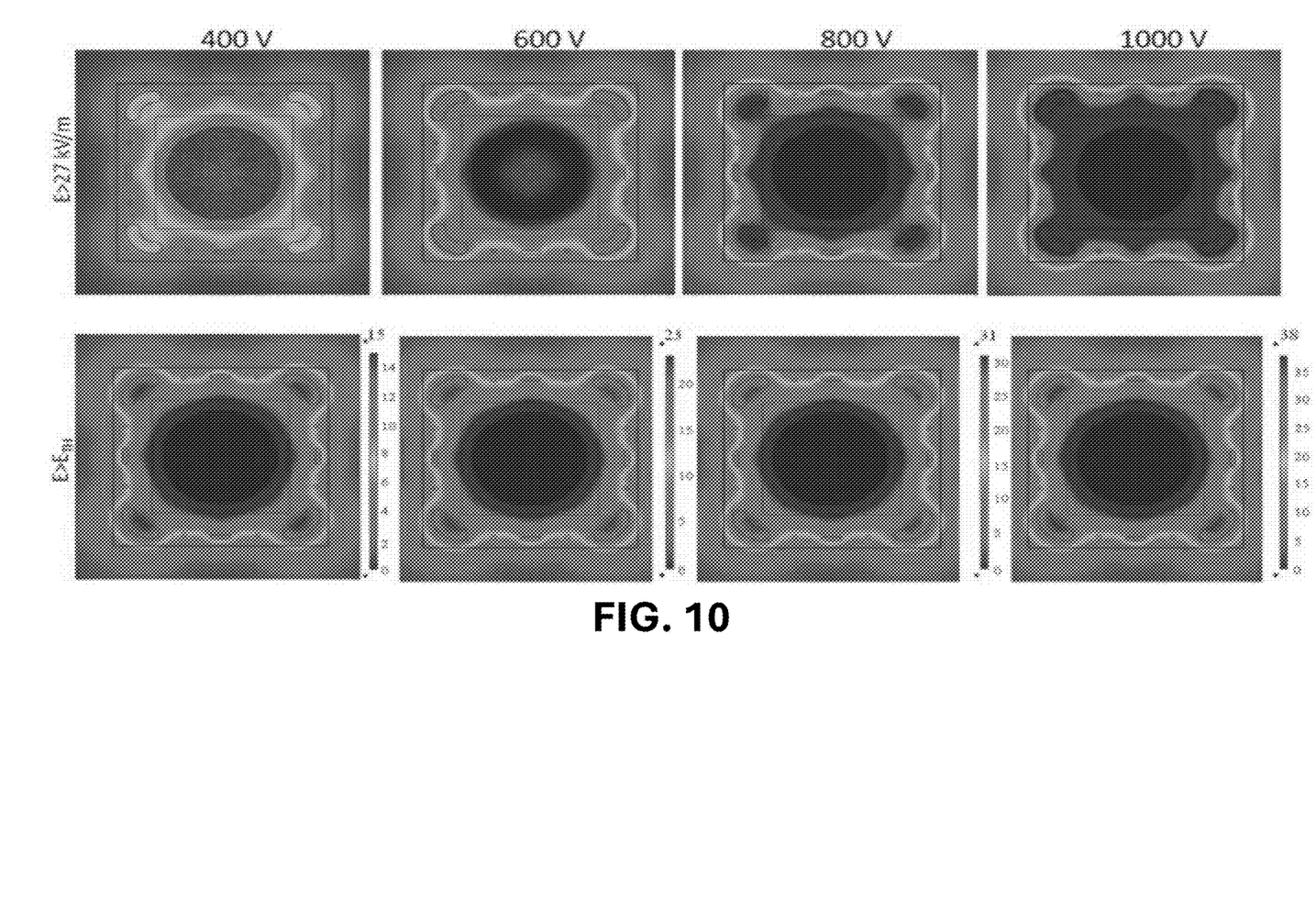
FIG. 10 illustrates some experimental results.

FIG. 10 illustrates some experimental results, obtained through multi-physics simulations, obtained by the topology of FIG. 9*c* and with side of 4 cm. The figure shows in which regions it is possible to obtain a field higher than 27 kV/m at a depth of 4 mm for different values of applied voltage. It is possible to notice how these regions are not convex for values of applied voltage lower than 800 V. It is recalled in this respect that in a Euclidean space a convex set is a set wherein, for each pair of points, the line segment joining them is entirely contained in the set.

In the second row of FIG. 10 it is observed how it is possible to identify, always at a depth of 4 mm, a convex region with diameter of 3 cm wherein E>ETH with ETH values decreasing for decreasing applied voltage. Particularly, ETH is equal to 15, 23, 31 and 38 kV/m, respectively, for pulses with amplitude of 400, 600, 800 and 1000 V.

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

Particularly, similar considerations apply if the flexible electrode and the electroporation device each one has a different structure or comprises equivalent components (for example, of different materials), or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

Moreover, the same solution may be implemented with an equivalent method (by using similar steps with the same functions of more steps or portions thereof, removing some steps being non-essential, or adding further optional steps); moreover, the steps may be performed in a different order, concurrently or in an interleaved way (at least in part).

The invention claimed is:

1. A flexible electrode for applying an electric field to a human body, the flexible electrode comprising:
   a gripping portion;
   a deformable structure having a first face fixed to the gripping portion and a flat second face opposite the first face, the deformable structure being compressible elastically between the first face and the second face for deforming to adapt a thickness thereof to a surface of a human body; and
   a flexible polymeric film arranged on the flat second face of the deformable structure and having an exposed flat face opposite the flat second face, wherein the flexible polymeric film is provided with flat metal structures defining at least one first electrode and one second electrode, the flat metal structures being embedded within the flexible polymeric film and comprising surfaces exposed from the flexible polymeric film being flush with the exposed flat face of the flexible polymeric film;
   wherein the deformable structure is configured to allow the first and second electrodes to adapt to a shape of a surface of a human body.

2. The flexible electrode according to claim 1, wherein the flexible polymeric film is provided with first through holes engaged by stems communicating electrically with the flat metal structures; the deformable structure having a plurality of second through holes aligned with the first through holes and housing thread-like electric conductors having first ends electrically interconnected with the stems and second ends communicating electrically with a signal supply cable of the flexible electrode.

3. The flexible electrode according to claim 1, wherein the gripping portion defines a flat wall on which the first face of the deformable structure is fixed firmly.

4. The flexible electrode according to claim 3, wherein the gripping portion comprises a rigid support defining the flat wall and a tubular handle provided externally with a grip and having an end portion connectable to an appendix that extends from the rigid support.

5. The flexible electrode according to claim 1, wherein the thickness of the deformable structure is constant in a direction perpendicular to a laying plane of the first face of the deformable structure and of the flat second face of the deformable structure.

6. The flexible electrode according to claim 1, wherein the thickness of the flexible polymeric film ranges from 0.2 to 5 mm.

7. The flexible electrode according to claim 1, wherein the flat metal structures defining the first electrode are arranged in a first area of the exposed flat face of the flexible polymeric film and are electrically connected to each other to be set to a common first potential whereas the flat metal structures defining the second electrode are arranged in a second area of the exposed flat face of the flexible polymeric film and are electrically connected to each other to be set to a common second potential different from the common first potential, the second area surrounding the first area without overlapping and without intersecting with the first area.

8. The flexible electrode according to claim 7, wherein the flat metal structures define a third electrode arranged in a third area of the exposed flat face of the flexible polymeric film and are electrically connected to each other to be set to the same potential of the first area or to a different third potential, the third area being external to the second area without overlapping and without intersecting with the second area and extending along a path that contains the first area internally.

9. The flexible electrode according to claim 1, wherein the deformable structure is made by a spongy structure, an elastomeric structure, or a flexible and compressible gel block.

10. An electroporation device comprising the flexible electrode according to claim 1 and a pulse generator adapted to generate pulses with adjustable amplitude to be fed to the flexible electrode for modifying a value of an electric field created in a tissue of a human body so that the value of the electric field exceeds a threshold value.

11. The electroporation device according to claim 10, wherein the threshold value is 20 KV/m in a convex area that penetrates within the tissue by at least 1 cm.

12. A method for producing a flexible electrode for applying an electric field to a human body, the method comprising:
   producing flat metal structures defining at least one first electrode and one second electrode being embedded within a flexible polymeric film and comprising surfaces exposed from the flexible polymeric film being flush with an exposed flat face of the flexible polymeric film;
   applying the flexible polymeric film onto a flat second face of a deformable structure with the exposed flat face of the flexible polymeric film opposite the flat second face of the deformable structure; and
   fixing a first face of the deformable structure opposite the flat second face of the deformable structure to a gripping portion, the deformable structure being compressible elastically between the first face and the second face for deforming to adapt the at least one first electrode and the at least one second electrode to a surface of a human body.

13. The method according to claim 12, wherein the flexible polymeric film is thermoplastic, the producing flat metal structures comprising:
  producing the flat metal structures being raised on the exposed flat face of the flexible polymeric film; and
  pressing the flexible polymeric film provided with the raised flat metal structures between heated flat molds being parallel to each other so that the flat metal structures penetrate into the flexible polymeric film such that the surfaces of the flat metal structures exposed from the flexible polymeric film are flush with the exposed flat face of the flexible polymeric film.

14. The method according to claim 13, wherein the producing the flat metal structures being raised comprises:
  preparing a silk-screen printing plate provided with through openings that define the geometry of the at least one first electrode and the at least one second electrode;
  superimposing and aligning the silk-screen printing plate with the flexible polymeric film provided with a plurality of through holes, the through openings of the silk-screen printing plate being arranged in correspondence to and facing the through holes of the flexible polymeric film;
  spreading a metallic paste onto the silk-screen printing plate so that the paste penetrates into the through openings of the silk-screen printing plate and into the through holes of the flexible polymeric film;
  removing the silk-screen printing plate thereby uncovering islands of the metallic paste that reproduce a perimeter of the through openings of the silk-screen printing plate on the flexible polymeric film;
  heating the flexible polymeric film provided with the islands of the metallic paste so that the metallic paste of the islands polymerizes and each island transforms into a corresponding one of the raised flat metal structures and the metallic paste arranged in the through holes polymerizes and produces corresponding metal stems; and
  thickening the raised flat metal structures by a galvanic deposition process.

15. The method according to claim 14, wherein the method comprises forming the through holes of the polymeric film by machining if the diameter of each through hole is higher than 0.3 mm or by laser if the diameter of each hole is lower than 0.3 mm.

16. The method according to claim 13, wherein the producing the flat metal structures being raised comprises:
  depositing the flat metal structures by a three-dimensional printer; and
  thickening the raised flat metal structures by a galvanic deposition process.

17. The method according to claim 12, wherein the method comprises providing an electric connection that crosses the deformable structure for connecting the at least one first electrode and the at least one second electrode electrically with a signal supply cable.

18. The method according to claim 12, wherein said producing the flat metal structures being raised comprises forming the flat metal structures defining the first electrode arranged in a first area of the exposed flat face of the flexible polymeric film electrically connected to each other to be set to a common first potential and forming the flat metal structures defining the second electrode arranged in a second area of the exposed flat surface of the flexible polymeric film electrically connected to each other to be set to a common second potential different from the common first potential, the second area surrounding the first area without overlapping and without intersecting with the first area.

19. The method according to claim 18, wherein said producing the flat metal structures being raised comprises forming the flat metal structures to define a third area of the exposed flat face of the flexible polymeric film being electrically connected to each other to be set to the same potential of the first area or to a different third potential, the third area being external to the second area without overlapping/intersecting with the second area.

* * * * *